United States Patent [19]

Saito et al.

[11] Patent Number: 5,237,103
[45] Date of Patent: Aug. 17, 1993

[54] PROCSSS FOR PREPARING CARBONYL COMPOUNDS

[75] Inventors: Yoshinori Saito; Masanori Tsuzuki; Hirotoshi Ishii, all of Chiba, Japan

[73] Assignee: Kemitsu Kosan Company Limited, Tokyo, Japan

[21] Appl. No.: 828,626

[22] Filed: Jan. 31, 1992

[30] Foreign Application Priority Data

Feb. 1, 1991 [JP] Japan .................................. 3-012029
Feb. 1, 1991 [JP] Japan .................................. 3-012030

[51] Int. Cl.$^5$ ............................................. C07C 45/34
[52] U.S. Cl. ................................. 568/360; 568/401; 568/475
[58] Field of Search ................ 568/360, 401, 473, 475

[56] References Cited

U.S. PATENT DOCUMENTS

| | | | |
|---|---|---|---|
| 3,365,498 | 1/1968 | Bryant et al. | 568/701 |
| 3,465,461 | 10/1969 | Lloyd et al. | 568/401 |
| 4,271,320 | 6/1981 | Takitoh et al. | 568/401 |
| 4,507,506 | 3/1985 | Shioyama | 568/101 |
| 4,550,212 | 10/1985 | Shioyama | 568/401 |
| 4,806,692 | 2/1989 | Yamada et al. | 568/401 |

FOREIGN PATENT DOCUMENTS

| | | | |
|---|---|---|---|
| 0418764 | 3/1991 | European Pat. Off. | 568/401 |
| 123085 | 12/1971 | Fed. Rep. of Germany . | |
| 51-117189 | 10/1976 | Japan . | |
| 62-223145 | 10/1987 | Japan . | |
| 63-500923 | 4/1988 | Japan . | |
| 1508331 | 4/1978 | United Kingdom . | |

OTHER PUBLICATIONS

Cum et al, J. Chem. Soc., Chem. Commun, pp. 1571–1573 (1985).
Chemical Abstracts, vol. 76, No. 7, 1972, Columbus, Ohio, US; abstract no. 33736S.
J. C. S. Chem. Comm. 1981, Letchworth, pp. 1274–1275.
Jan-E. Backvall et al, J. Am. Chem. Soc., vol. 112, pp. 5, 160–5, 166 (1990).

*Primary Examiner*—James H. Reamer
*Attorney, Agent, or Firm*—Armstrong, Westerman, Hattori, McLeland & Naughton

[57] ABSTRACT

The process for preparing the carbonyl compound involves oxidizing the olefins in the presence of the catalyst composed of the palladium compound and the polyoxoanion compound in a mixture of water with a cyclic ether having at least a dioxane ring or a dioxolan ring or in the presence of the catalyst composed of the palladium compound, the polyoxoanion compound and the quinone and/or the aromatic diol in a solvent. This process yields carbonyl compounds, such as ketones and aldehydes, useful as solvents, raw chemicals and so on, with a high production rate per unit time and unit palladium quantity.

12 Claims, No Drawings

PROCSSS FOR PREPARING CARBONYL COMPOUNDS

BACKGROUND OF THE INVENTION

1. Field of the Invention

The present invention relates to a process for preparing carbonyl compounds and, more particularly, to a process for efficiently and stably preparing carbonyl compounds including ketones, particularly such as methyl ethyl ketone, methyl isobutyl ketone, acetone, cyclopentanone, etc., and aldehydes, such as acetaldehyde, etc., by oxidizing olefins. The carbonyl compounds are useful as solvents, raw chemical materials and so on.

2. Description of the Released Art

Carbonyl compounds including ketones such as methyl ethyl ketone, methyl isobutyl ketone, acetone, etc. and aldehydes such as acetaldehyde, etc. are useful as solvents and raw chemical materials and so on.

As the method for the preparation of the carbonyl compounds by the direct oxidation of olefins, there is known the Wacker type oxidation process in which $PdCl_2$—$CuCl_2$ is employed as a catalyst. The Wacker type process requires a relatively large quantity of an active chlorinated compound so that it causes the problems with corrosion of equipment, by-production of chlorinated compounds, and so on. Further, the Wacker type oxidation has the defects that a reaction rate is decreased to a remarkable extent as the number of carbons of raw olefin materials increases, and that the reactivity of the internal olefins is low, so that the Wacker type process is industrially applicable only to the production of lower carbonyl compounds such as acetoaldehyde, acetone and so on.

In order to solve those problems, various process have recently been proposed in which catalysts of a new type are employed, in place of a so-called Wacker type catalyst. Those processes, however, are said to be industrially insufficient.

For example, Japanese Patent Laid-Open Publication (kokai) No. 51-117,189 discloses a process in which there is employed a catalyst composed of a combination of a Pd compound with a heteropolyacid or with an isopolyacid.

As the conventional process employs water as a solvent, however, it suffers from the disadvatnages that the reaction rate becomes low, productivity becomes poor, and so on. The reason for the low reaction rate is because of the raw olefin material employed is less soluble in a solution containing catalyst (an aqueous solution) and the efficiency in the contact of the raw olefin material with the solution containing catalyst (or a catalyst component) becomes remarkably poor. In addition, this conventional process employs a largely excessive quantity of the heteropolyacid or isopolyacid, relative to the palladium compound, so that a large quantity of the heteropolyacid or the isopolyacid is required in order to ensure the sufficiently high reaction rate. This is disadvantageous in terms of economy and this is further a cause of various problems as will be described hereinafter.

It is to be noted that this conventional process can reduce the problem with corrosion of equipment to a considerably low level, as compared with the Wacker type process which requires a large quantity of the active chlorinated compounds, particularly $CuCl_2$ or hydrochloric acid, however, the problem with corrosion of equipment cannot be said to be solved to a sufficient extent. In fact, this conventional process requires the use of an anti-corrosive agent, such as polyethyl siloxane and so on, and the adjustment of pH of a solution containing catalyst with sulfuric acid to, for example, pH=1. Further, the heteropolyacid and the isopolyacid are remarkably lower than $CuCl_2$ or hydrochloric acid in terms of the extent to which equipment causes corrosion. However, they are an acidic compound so that this conventional process suffers from the disadvantage that a large quantity of highly concentrated aqueous solution should be employed. This is disadvantageous in terms of complete prevention of corrosion of equipment and further the use of sulfuric acid is disadvantageous in terms of prevention of corrosion of equipment.

In addition, the conventional process is likely to cause isomerization of olefins. When the raw material to be employed is an olefin having a long chain, the problems are that the reactivity becomes low and the selectively to the objective carbonyl compounds becomes low. For instance, when 1-hexene is employed as the raw material, the isomerization to 2-hexene is promoted and, as a result, the reactivity is so lowered that the conversion and the selectivity to 2-hexanone are caused to be lowered, thereby increasing the by-production of 3-hexanone. The cause that the isomerization is likely to occur is considered to result from the fact that only water is employed as the solvent and that a large quantity of the heteropolyacid or the isopolyacid is employed.

Further, U.S. Pat. No. 4,550,212 discloses a process in which the reaction is carried out in a two-phase solvent composed of decane and water by using a multi-component catalyst, such as a catalyst capable of transferring between phases, obtainable by adding $H_3BO_3$ or cetyltrimethylammoniumbromide (a surfactant) to a Pd-heteropolyacid system.

This process takes advantage of the technology of reaction using a catalyst of such a type as transferring between phases in order to improve the efficiency in the contact of the raw olefin material, concentrated by dissolving it mainly in the decane phase, with the catalyst component that exists mainly on the side of the aqueous solution via the action of the surfactant.

It is to be noted, however, that this conventional process basically employs a two-phase type solvent composed of decane and water, which are not incompatible with each other. Hence, this conventional process presents the problems that the efficiency in the contact between the raw olefin material and the catalyst is insufficient and the reaction rate is slow. Further, this process has the defect that the reactivity of 2-butene is lower than that of 1-butene. In addition, this conventional process is of a multi-component system in which the reaction system is complex, so that it presents the drawbacks that the separation and recovery of the product, solvent, catalyst components and so on are laborious.

In addition, Patent Laid-open Publication (kohyo) No. 63-500,923 proposes a process using a catalyst system in which a redox metal, such as Cu, Fe, Mn or the like, and/or ligand (acetonitrile or the like) are added to a Pd-polyoxoanion system.

In this case, however, the addition of either of the redox metal or the ligand provides merely the small effect of improvements in the catalyst activity and the improvements in the catalyst activity depends largely upon the synergy between the redox metal and the ligand. Hence, the problems are that the catalyst system becomes complex as a matter of course as well as the separation and recovery of the catalyst components and so on are as laborious as the other conventional process as described hereinabove. Further, this conventional process presents the severe problem that the sedimentation of the catalyst component is caused to occur as the reaction proceeds, thereby lowering the reaction rate to a remarkably low level, although the reactivity in the initial stage of the reaction is relatively good.

Further, Japanese Patent Laid-Open Publication (kokai) No. 62-223,145 proposes a process in which the reaction is carried out in a solvent containing a carbamoyl group in the presence of a catalyst system obtainable by adding water to a Pd-redox metal salt-quinone catalyst.

This process, however, presents the problems that the reactivity is low and, if the raw olefin material is an internal olefin, the reactivity becomes lower than when the raw olefin material is a terminal olefin.

In addition, Jan-E. Backvall et al., J. Am. Chem. Soc., vol. 112, pages 5,160–5,166 (1990) proposes a process using a catalyst composed of a Pd-polycyclic metal-quinone-perchloric acid system. Fe-porphyrin is the most useful as the polycyclic metal to be employed in this process.

This conventional process employed, however, is extremely small in scale, although the reaction rate is improved, as compared with the usual Wacker type process. Further, this process causes the isomerization to occur from the terminal olefin to the internal olefin due to the presence of a perchloric acid and these the internal olefin are less inreactivity. In addition, this process presents the drawback that the Pd settles rapidly in the absence of the acid. Moreover, porphyrin compounds, using in this reaction system, are known to be unstable in general.

As described hereinabove, those conventional processes, however, have the drawbacks as described hereinabove, so that they are not yet practically applicable on an industrial scale. Demands have been strongly made to develop improvements in technology that can solve those problems and realize industrialization with ease.

The present invention has been performed on the basis of the situation as described hereinabove.

SUMMARY OF THE INVENTION

The object of the present invention is to solve the problems inherently in the conventional processes as described hereinabove and to provide a process for preparing carbonyl compounds with high efficiency and productivity in preparing the carbonyl compounds, such as aldehydes and ketones, by oxidizing olefins with the aid of a catalyst system composed of Pd compounds and the polyoxoanion compounds such as heteropolyacids or isopolyacids in the presence of a cyclic ether containing a dioxane ring and/or a dioxalan ring and water by sufficiently improving the reactivity of the olefins to the carbonyl compounds (the reactivity of ethylene to acetaldehyde and of propylene to acetone as well as the reactivity particularly of a higher olefin such as butene or the like or of internal olefins such as 2-butene or the like to the corresponding ketones) and by maintaining the substantial catalyst activity and the reaction rate at a high and stable level while preventing sedimentation of the catalyst components or deterioration of the activity due to aggregation.

Another object of the present invention is to solve the problems inherently in the conventional processes as described hereinabove and to provide a process for preparing carbonyl compounds with favorable efficiency and productivity by oxidizing the olefins in the presence of a catalyst system composed of the palladium compound, the polyoxoanion compounds having two different valency anion and a quinone and/or an aromatic diol, to imprive the reactivity of the olefins to the carbonyl compounds, such as the ketones or aldehydes, to maintain stably the substantial catalyst activity at a high level, and to prevent the catalyst components from settling.

The present invention has been completed on the basis of the object as described hereinabove.

In a first preferred mode according to the present invention, the process for preparing a carbonyl compound is characterized by oxidizing an olefin with the aid of a catalyst composed of the palladium compounds and the polyoxoanion compounds in the presence of a cyclic ether containing a dioxane ring and/or a dioxolan ring and water.

In a second preferred mode according to the present invention, the process for preparing a carbonyl compound is characterized by oxidizing an olefin with the aid of a catalyst composed of the palladium compounds, the polyoxoanion compounds having two different valency anion and a quinone and/or an aromatic diol in the presence of a solvent.

The process according to the present invention is remarkably advantageous because it does not require a largely excessive quantity of the polyoxoanion compounds, it does not cause any corrosion of equipment, and it facilitates the separation of the product and so on from the reaction system as well as the separation, recovery and reuse of the solvent, catalyst or their components.

Other objects, features and advantages of the present invention will become apparent in the course of the detailed description of the preferred embodiments, which follow.

DETAILED DESCRIPTION OF THE PREFERRED EMBODIMENTS

First Mode

Catalyst

The catalyst to be employed in the first mode of the process according to the present invention comprises the palladium compound and the polyoxoanion compounds.

As the palladium compounds, there may be used any compound as long as it contains Pd as a metallic components and it includes various compounds as have been employed commonly in this field.

Specifically, as the palladium compounds, there may be mentioned various inorganic palladium compounds or complexes including, for example, palladium sulfate, palladium nitrate, palladium carbonate, palladium-containing polyoxoanion compound such as a palladium salt of a heteropolyacid, a palladium salt of an isopolyacid, etc., a palladium halide such as palladium chloride, palladium bromide, etc., an alkali metal palladate such as sodium tetrachloro-palladate, sodium tetrabromopalladate, potassium tetra-chloropalladate, potassium tetrabromopalladate, etc., an amine complex compound such as $Pd(NH_3)_4Cl_2$, palladium hydroxide, palladium oxide, and so on; various organic palladium compounds or complexes including, for example, a palladiumu salt of an organic acid such as palladium acetate, etc., a palladiumacetylacetonate, a palladium nitryl complex such as $Pd(CH_3CN)_2Cl_2$, $Pd(PhCN)_2Cl_2$ (wherein Ph represents a phenyl group), etc., a palladium phosphine complex such as $Pd(PPh_3)_4$, etc., a palladium amine complex compound such as $Pd_2(dba)_3CHCl_3$ (wherein dba represents dibenzylidene acetone), $Pd(cod)Cl_2$ (wherein cod represents cyclooctadiene), Pd(edta) (wherein edta represents ethylenediaminetetraacetic acid), etc.; and an active metallic palladium such as palladium colloid, highly dispersed palladium metal, etc.

Among these palladium compounds, there may preferably by usually employed the palladium compounds containing a divalent palladium (having the oxidation number of +2). Particularly, $PdSO_4.2H_2O$ is preferably employed.

The palladium compounds may be employed in various forms, for example, in the form of an anhydride, in the form containing crystalline water, in the form of a solution such as an aqueous solution, a solution dissolved in an organic solvent, etc., in the form of a suspension or in the form in which the palladium compounds are deposited on a carrier such as active carbon, etc. The palladium compounds may be employed singly, in a mixture of two compounds or more or in the form of a compound material or a composition.

The polyoxoanion compounds are not restricted to any particular polyoxoanion compounds as long as they can readily oxidize the reduced-state Pd into the oxidized-state Pd (particularly $Pd^{2+}$) in the catalyst cycle and the resulting polyoxoanion compounds in the reduced state can readily be re-oxidized with the aid of an oxidizing agent, such as oxygen or the like. The polyoxoanion compounds contain a metal having at least two different valency state upon dissociation into ions on the anion. There may be employed various known compounds which are employed commonly in this field.

As the polyoxoanion of the polyoxoanion compounds, there may be mentioned ones containing one or more than one metal component selected from V, Mo, W, Nb, Ta and so on. Further, the polyoxoanions may be heteropolyoxoanions or isopolyoxoanions. In addition, when the polyoxoanion has one kind of the metal component, the one containing Mo or V is preferred. When the polyoxoanion is composed of two or more than two kinds of the metal components, the one containing two kinds of Mo and V, Mo and W or V and W is preferred or the one containing three kinds of Mo, W and V is preferred.

The above mentioned heteropolyoxoanion is of such a structure that a hetero atom selected from various hetero atoms, such as P, Si, As, Ge, B, Se, Te and so on, is contained in the structure of the polyoxoanion.

In the process according to the present invention, there may be employed the heteropolyoxoanion containing those various hetero atoms as described hereinabove. Particularly, the heteropolyoxoanion containing P as the hetero atom is preferred.

Specifically, preferred examples of the polyoxo anions may include heteropolyoxoanions, such as $[PV_2Mo_{10}O_{40}]^{5-}$, $[PV_3Mo_9O_{40}]^{6-}$, $[PV_4Mo_8O_{40}]^{7-}$, $[PV_6Mo_6O_{40}]^{9-}$, $[PV_8Mo_4O_{40}]^{11-}$, $[PMo_6W_6O_{40}]^{3-}$, $[P_2VMo_2W_{15}O_{62}]^{7-}$, $[PV_3W_7O_{40}]^{6-}$, $[P_2VMo_5W_{12}O_{62}]^{7-}$, $[PMo_{12}O_{40}]^{3-}$, and so on, and isopolyoxoanions, such as $[Mo_3V_3O_{19}]^{5-}$, $[V_2Mo_6O_{26}]^{6-}$, $[V_4Mo_8O_{36}]^{4-}$, $[V_6Mo_6O_{36}]^{6-}$, $[V_8Mo_4O_{36}]^{8-}$, $[V_2Mo_3W_7O_{36}]^{2-}$, and so on.

As the polyoxoanion compounds, there may be mentioned compounds composed of the aforesaid heteropolyoxoanion or isopolyoxoanion and one or more than one positive ion component (a counter cation). In other words, the polyoxoanion compounds may be a heteropolyacid, a isopolyacid or a salt thereof.

The polyoxoanion compounds may contain crystalline water. As the positive ion component (the counter cation), there may be mentioned $H^+$, $NH^{4+}$, $Li^+$, $Na^+$, $K^+$, $Rb^+$, $Cs^+$, $Pd^{2+}$, $Rh^{3+}$, and so on. Among these ions, $H^+$ is particularly preferred.

The polyoxoanion compounds may include various ones in accordance with the kind of and combination of the polyoxoanions and the positive ion components, and any one of those polyoxoanion compounds may be employed. Among these polyoxoanion compounds, the heteropolyacid consisting of the aforesaid heteropolyoxoanion and $H^+$ is preferred in terms of the catalyst activity.

As particularly preferred examples of the heteropolyacids, there may be mentioned $H_3[PMo_2O_{40}]$, $H_5[PV_2Mo_{18}O_{40}]$, $H_6[PV_3Mo_9O_{40}]$, $H_7[PV_4Mo_8O_{40}]$, $H_9[PV_6W_6O_{40}]$, $H_9[PMo_6W_8O_{40}]$, $H_{11}[PMo_4V_8O_{40}]$, $H_3[PMo_6W_8O_{40}]$, $H_7[PMo_6V_6O_{40}]$, $H_6[PV_3W_9O_{40}]$, $H_7[P_2VMO_2W_{15}O_{62}]$, $H_7[P_2VMo_5W_{12}O_{62}]$, and so on.

The polyoxoanion compounds, such as those aforesaid heteropolyacids, may be employed in various forms, for example, in the form of an anhydride, in the form containing crystalline water, in the form of a solution such as an aqueous solution, a solution dissolved in an organic solvent, etc., in the form of a suspension or in the form in which the polyoxoanion compounds are deposited on a carrier such as active carbon, etc. The polyoxoanion compounds may be employed singly, in a mixture of two compounds or more or in the form of a compound material or a composition.

The catalyst to be employed for the process according to the present invention comprises at least one or more than one aforesaid palladium compound and at least one or more than one aforesaid polyoxoanion compound. These catalyst components may be supplied to the reaction system separately or in the form of a mixture. It is to be noted herein that a palladium salt of the heteropolyacid or a palladium salt of the isopolyacid may be employed as in the aforesaid palladium compound or the aforesaid polyoxoanion compound or both of thereof.

The rates of the polyoxoanion compound and the palladium compound to be employed for forming the catalyst may be chosen in accordance with the kind of and the combination of those compounds. The polyoxoanion may range usually from 0.5 mole to 100 moles, preferably from 1 mole to 20 moles, 1 per mole of the palladium component in the palladium compound.

When the rate of the polyoxoanion is smaller than 0.5 mole per 1 mole of the palladium component, on the one hand, the re-oxidation of the reduced type palladium component into the oxidized type palladium component in the catalyst cycle cannot be performed to a sufficient extent, thereby failing to maintain the catalyst activity at a high level. When the rate of the polyoxoanion is larger than 100 moles per 1 mole of the palladium component, on the other hand, undesirable by-products are likely to be formed and such a large amount of the polyoxoanion is economically disadvantageous.

It is further to be noted that the catalyst may contain other co-catalyst component (including a ligand component), if desired, within the range that does not adversely affect the objects of the present invention.

In the process according to the present invention, the catalyst may be employed in a homogeneous state, in a heterogeneous state or in a state which is composed homogeneous state and heterogeneous state, when it is employed in the presence of the cyclic ether and water. For instance, the catalyst may be employed in the form of a homogeneous solution in which the catalyst components are dissolved in a mixture solvent composed of the cyclic ether and water or in the form in which a portion of the catalyst components are dissolved in the mixture solvent and the other portion thereofis dispersed in the mixture solvent. Further, a portion or a whole of the catalyst components may be employed in the form in which it is deposited or fixed on an appropriate carrier such as active carbon, silica, a polymer or the like.

Materials existing together with the catalyst (cyclic ethers and water or solvents thereof)

In accordance with the present invention, it is of significance that the oxidation of the olefins is carried out with the aid of the catalyst in the presence of at least a mixture of the cyclic ether having a dioxane ring and/or a dioxolan ring with water.

It is to be noted herein that the process according to the present invention usually employs a catalyst solution, preferably a homogeneous solution containing catalyst, composed of a mixture of the solvents consisting of the cyclic ether and water with the catalyst when the process is carried out in a liquid phase, although the conventional processes are carried out in a catalyst solution (an aqueous solution) using water as a solvent. However, the process according to the present invention can be carried out in a gaseous phase, particularly in a vapor phase passage system, in which the catalyst is employed in the state, for example, in which the catalyst is deposited or fixed on the carrier such as active carbon or the polymer. Hence, in this case, each of the cyclic ether and water may be supplied to the reaction system in a gaseous state or in any state that can comply with the catalyst in a solid state. In other words, the cyclic ether and water are not restricted to the case that they are supplied as solvents for the catalyst components, when they are employed as materials existing together with the catalyst, and they may be supplied in various forms and in various supply systems, neither in restricted states nor in restricted supply systems.

As described hereinabove, the catalyst is used in the presence of the materials existing together with the catalyst, such as solvents composed of at least water and the cyclic ether having the dioxane ring and/or the dioxolan ring, not with water alone, thereby improving the velocity of producing the carbonyl compounds from the various olefins with a remarkable extent. Further, the high production velocity can be maintained in a stable manner, thereby achieving the objects of the present invention.

In other words, by using the catalyst together with the materials existing with the catalyst, such as the solvents containing the particular cyclic ether as well as water, the process according to the present invention can suppress the sedimentation or aggregation of the catalyst components as the reaction proceeds, which is the problem in the conventional processes. Further, the process according to the present invention can maintain the catalyst performance, i.e. the catalyst activity and selectivity, at a high level and in a stable manner and further improve the efficiency in the contact between the olefin and the catalyst with a remarkable extent.

As the dioxane ring of the cyclic ethers, there may be mentioned a 1,4-dioxane ring and a 1,3-dioxane ring. These dioxane rings may be unsubstituted or substituted at least with one substituent such as an alkyl group. As the dioxolan ring, a 1,3-dioxolan ring is preferred, and it may be unsubstituted or likewise substituted.

As the cyclic ethers, there may be usually employed a cyclic ether composed of one dioxane ring or one dioxolan ring. It is to be noted herein that there also may be employed a cyclic ether composed of two or more than two dioxane rings or two or more than two dioxolan rings or a cyclic ether composed at least of one dioxane ring and one dioxolan ring.

Typical examples of the cyclic ethers may include 1,4-dioxane, an alkyl-substituted 1,4-dioxane, 1,3-dioxane, an alkyl-substituted 1,3-dioxane, 1,3-dioxolan, an alkyl-substituted 1,3-dioxolan, and so on.

The alkyl substituent of each of the alkyl-substituted dioxanes and the alkyl-substituted dioxolans is not restricted to a particular one and it may be linear or branched or of a cyclic structure such as a cycloalkyl group or a cycloalkylalkyl group or a araklyl group. Usually, the alkyl substituent may preferably include, for example, a lower alkyl group having from one to about four carbon atoms, such as methyl, ethyl, n-propyl, isopropyl, n-butyl, isobutyl, sec-butyl, tert-butyl, etc., and so on, when the compatibility and affinity of the cyclic ethers with water are taken into account. Among the alkyl substituents, methyl and ethyl are particularly preferred.

The number of the alkyl substituents of the alkyl-substituted dioxanes and the alkyl-substituted dioxolans and the position of the alkyl substituents thereof are not restricted to particular ones, however, the number of the alkyl substituents thereof is preferably one or two, particularly preferably one, in terms of the compatibility and affinity with water. Representative examples of the dioxanes and dioxolans substituted with one alkyl substituent may include 2-alkyl-1,4-dioxane, 2-alkyl-1,3-dioxane, 4-alkyl-1,3-dioxane, 5-alkyl-1,3-dioxane, 2-alkyl-1,3-dioxolan, 4-alkyl-1,3-dioxolan, and so on.

It is to be noted herein that the cyclic ethers have the compatibility and have the affinity with water, because they have the dioxane ring and/or the dioxolan ring. This property plays a significant role in achieving the objects of the present invention to a sufficient extent, particularly when the cyclic ether and water are employed as liquid solvents. The extent of the compatibility and affinity with water may vary with the presence or absence of the substituent on the dioxane ring or the dioxolan ring and the kind of the substituent, i.e. the size of the alkyl substituent, and so on. In the process according to the present invention, there may favorably employed the cyclic ethers having a higher affinity with water, preferably having a higher compatibility with water. As it is commonly known that the cyclic ethers are generally superior in solubility in a hydrocarbon, such as an olefin, or an organic compound, this property is of significance in achieving the objects of the present invention to a sufficient extent, when the cyclic ethers and water are employed as liquid solvents.

Preferable examples of the specific cyclic ethers include 1,4-dioxane, 1,3-dioxane, 2-methyl-1,4-dioxane, 2-ethyl-1,4-dioxane, 2-methyl-1,3-dioxane, 2-ethyl-1,3-dioxane, 4-methyl-1,3-dioxane, 4-ethyl-1,3-dioxane, 5-ethyl-1,3-dioxane, 1,3-dioxolan, 2-methyl-1,3-dioxolan, 2-ethyl-1,3-dioxolan, 4-methyl-1,3-dioxolan, 4-ethyl-1,3-dioxolan and so on. Among these examples, 1,4-dioxane, 1,3-dioxane, 1,3-dioxolan, 2-methyl-1,3-dioxolan, etc. are preferred.

The various cyclic ethers may be employed singly or in combination with two or more as the component for the material existing together with the catalyst or as the component for the solvent.

The rate of the cyclic ether with respect to water in the material existing together with the catalyst, such as the solvents, is not restricted to a particular one and it may arbitrarily be chosen with the following taken into account. In other words, the appropriate rate of the cyclic ether with respect to water may be determined on the basis of the kind of the catalysts or their ingredients, i.e. the palladium compounds or the polyoxoanions, the kinds of the raw olefins and the cyclic ethers, reaction systems, reaction conditions and so on, although it may vary with these elements and it cannot be determined in a uniform way. Further, it should be taken into account that an extremely low quantity of water reduces solubility of the catalyst components or the reaction rate becomes low due to the reason for reaction mechanism. On the other hand, if the water content becomes extremely large, the Pd component settles as a metallic palladium ($Pd^\circ$) or aggregates, thereby causing the likelihood to reduce the catalyst activity. In addition, as the solubility of the raw olefins into water is so low, the problem may arise that the efficiency in contact between the raw olefins and the catalyst (the solution containing catalyst) is so lowered, particularly in the liquid-phase reaction, that the sufficient reaction rate cannot be achieved. From these reasons, the material existing together with the catalyst, particularly water, is employed at the rate ranging usually from 5% to 70% by weight, preferably from 10% to 50% by weight, in the solvent mixture. It is further noted that the materials existing together with the catalyst, such as the solvents, may contain other solvent components such as, for example, an alcohol, a hydrocarbon, an ether, an ester, a ketone or a nitrile, unlessimproving the objects of the present invention.

In the process according to the present invention, the solvents may be employed in any form as long as they are employed as the materials existing together with the catalyst. For example, the solvents may be employed as solvents for making the catalyst a homogeneous solution or as dispersing the catalyst or in such a state that they are contained in the catalyst or in the catalyst components.

When the catalyst or the catalyst component is dissolved or dispersed in the solvent mixture consisting of the cyclic ether and water, the rate of the solvent mixture may be in the range usually from approximately 1 liter to 10,000 liters per 1 mole of the palladium component to be employed.

Raw Olefins

The olefins to be employed for the process according to the present invention are not restricted to particular ones as long as they contain at least one olefinic double bond (C=C), and they may include, for example, an olefin having a plurality of olefinic double bonds, such as a diene, a triene, and so on, in addition to a mono-olefin. Further, the olefins may contain a terminal olefin having the olefinic double bond (C=C) at its terminal position, an internal olefin having the olefinic double bond (C=C) at its internal position, and an olefin having the olefinic double bonds at both of its terminal and internal positions.

In addition, the olefins may be a linear olefin such as a linear alkene, a linear alkadiene or the like or a cyclic olefin having a cyclic substituent, such as a cyclic olefin, e.g. a cycloalkene, a cycloalkadiene or the like, a cycloalkyl group, an aromatic group, or the like.

The number of carbon atoms of the olefins is not restricted to a particular one as long as the number of carbon atoms is two or more. The number of the carbon atoms thereof usually ranges from 2 to 20, preferably from 2 to approximately 10.

The linear olefins may be a straight-chain olefin or a branched-chain olefin. As the linear olefins, there may specifically mentioned, for example, a mono-olefin including ethylene, propylene, 1-butene, trans-2-butene, cis-2-butene, isobutene, 1-pentene, 2-pentene, 3-methyl-1-butene, as isopentene such as 2-methyl-2-butene or the like, 1-hexene, 2-hexene, 3-hexene, 3-methyl-1-pentene, 4-methyl-1-pentene, an isohexene such as 4-methyl-2-pentene or the like, neohexene, 1-heptene, 2-heptene, 3-heptene, 4-methyl-1-hexene, an isoheptene such as 5-methyl-2-hexene, 1-octene, 2-octene, 3-octene, 4-octene, isooctene, 1-nonene, 2-nonene, isononene, 1-decene, 2-decene, 3-decene, 4-decene, 5-decene, isodecene, undecene, dodecene, tridecene, tetradecene, hexadecene, and so on, and a diene including a pentadiene, a hexadiene, a heptadiene, an octadiene, a decadiene, and so on.

Specific examples of the cyclic olefins may include a cycloalkene such as cyclopentene, cyclohexene, cyclooctene, cyclodecene and so on, a cycloalkadiene such as cyclooctadiene and so on. Further, the cycloalkenes and the cycloalkadienes may be substituted with a substituent such as an alkyl substituent.

The olefins having the aromatic group may include, for example, various compounds in which an aryl group such as a phenyl group or an alkyl phenyl group is substituted on the various linear olefins or the cyclic olefins. As typical examples of the olefins having the aromatic substituent, there may be mentioned, for example, a styrene type hydrocarbon such as styrene, p-methylstyrene, β-methylstyrene and so on.

As the olefins having other cyclic structure, there may be mentioned, for example, vinylcyclohexane, vinylcyclohexene, allylcyclohexane and so on.

As the specific examples of the olefins that can be employed particularly favorably, there may be mentioned, for example, ethylene, propylene, 1-butene, trans-2-butene, cis-2-butene, 1-pentene, 2-pentene, isopentene, 1-hexene, 2-hexene, 3-hexene, 4-methyl-1-pentene, isohexene, neohexene, 1-heptene, 2-heptene, 1-octene, 2-octene, isooctene, cyclopentene, cyclohexene, cyclooctene, sytrene, and so on.

As described hereinabove, the process according to the present invention can realize the high reactivity for the internal olefins such as 2-butene and the cyclic olefins such as cyclopentene, as well as the α-olefins (terminal α-olefins).

In the process according to the present invention, the olefins as the hydrocarbons are usually employed as the raw materials, however, the olefins containing a hetero atom may also be employed as the raw materials unless improving the objects of the present invention.

Further, the various olefins may be employed singly or in combination with two or more than two olefins. In addition, the raw olefins may contain other components that do not adversely affect the objects of the present invention. The olefins may be supplied to the reaction system, as needed, in a mixture with water or other solvents.

Oxidizing Agents

In the process according to the present invention, the oxidizing agents to be employed for the oxidation of the olefins may usually include, for example, oxygen gases and mixed gases of oxygen gases and a dilute gas, such as oxygen-enriched air, air, etc. As the dilute gas, there may be usually employed, for example, nitrogen gas, although the dilute gas is not restricted to a particular one, and it may further include, for example, helium, argon, carbon dioxide and so on. In addition, the oxygen and oxygen-containing gases may contain other ingredients as long as they do not adversely affect the objects of the present invention. The gases to be employed as the oxidizing agents may be supplied to the reaction system, as desired, in such a system as containing other ingredients such as moisture or solvent components.

Oxidation

The process according to the present invention synthesizes the carbonyl compounds, i.e. the ketones and-/or aldehydes, by oxiding the corresponding olefins with the aid of the catalyst in the presence of the materials existing together with the catalyst.

The reaction system is not restricted to a particular one as long as the olefins can be treated with the aid of the catalyst in the presence of the material existing together with the catalyst. The reaction system in the vapor phase reaction and/or in the liquid phase reaction may include, for example, a batch system, a semi-batch system, a semi-continuous system, a continuous system or a system in which the aforesaid systems are combined.

As described hereinabove, the catalyst can be employed in the various states, that is, in a homogeneous state (in a homogeneous solution containing catalyst) in which the catalyst is dissolved in the solvent, in a heterogeneous state (in a heterogeneous solution containing catalyst) in which only a portion of the catalyst is dissolved in the solvent while the rest of the catalyst is dispersed therein or in a heterogeneous state (in a solid state) in which the catalyst is deposited or fixed on a carrier or a polymer.

The raw olefins, the catalysts and the solvents or the materials existing together with the catalysts may be supplied each in a liquid state or in a gaseous state. In other words, they can be supplied in a system, for example, in which a solution having catalyst obtainable by admixing the catalyst with the solvent or a mixture of the resulting solution having catalust with the olefin is used in a liquid phase and the reactions carried out in a batch system, in which the olefin in a gaseous state and the gases (oxygen gases or oxygen-containing gases) as the oxidizing agent are introduced into the solution having catalyst or the gases as the oxidizing agent are introduced into a mixed solution composed of the catalyst solution and the olefin, in which the catalyst solution, the olefins and the oxidizing gases are introduced simultaneusly into a reaction region, or in which the catalyst component is deposited or fixed to the carrier or the polymer in a heterogenous state (in a solid state) and the gaseous olefin, the oxidizing gases and solvent vapors (gaseous materials existing together with the catalyst) are exposed in gaseous state to the catalyst component in the solid state.

When the reaction is carried out in a batch system, the rate of the raw olefins with respect to the catalyst may appropriately range usually from 1 mole to 10,000 moles, preferably from 10 moles to 5,000 moles, per 1 mole of the palladium component to be employed, although it cannot be determined in a constant manner because it depends upon the activity of the catalyst and other reaction conditions. If the rate is too small, on the one hand, the productivity with respect to the catalyst unit becomes too low and it is economically disadvantageous. If the rate becomes too large, on the other hand, no sufficient rate of selectivity may be achieved or the reaction may take a longer time.

When the reaction is carried out in such a liquid or gaseous phase system that the olefin and the oxidizing gases are continuously supplied to the solution having the catalyst or to the solid catalyst layer, the rate of the raw olefin to be supplied per 1 mole of the palladiumu component may appropriately range usually from approximately 10 moles to 5,000 moles per hour.

The reaction temperature may appropriately be set within the range usually from 0° C. to 200° C., preferably from 20° C. to 100° C., when the reaction is carried out in the liquid phase system. If the reaction temperature is below 0° C., the reaction rate may become too low. When the reaction temperature exceeds 200° C., by-products are likely to occur.

When the reaction is carried out in the gaseous phase system, the reaction temperature may appropriately range usually from 50° C. to 700° C., preferably from 100° C. to 500° C. If the reaction temperature is below 50° C., on the one hand, the reaction rate may become too low. If the reaction temperature is above 700° C., on the other hand, by-products are likely to be formed.

The reaction pressure may economically range usually from ambient pressure to approximately 100 kg/cm$^2$ although it may be chosen within a wide scope in the range from ambient to high pressure.

Reaction Product

As described hereinabove, the carbonyl compounds, such as the ketones, the aldehydes or mixtures thereof, can be produced from the corresponding olefins in a stable manner with high efficiency.

For example, when ethylene is employed as a raw material, acetaldehyde is yielded as a reaction product. Further, when propylene is employed as a raw material, acetone is yielded as a reaction product. In addition, 1-butene, 2-butene or a mixture thereof yields methyl ethyl ketone, and 4-methyl-1-pentene yields methyl isobutyl ketone.

The carbonyl compounds as the reaction products yielded in the manner as described hereinabove may be separated, isolated and purified in conventional manner, thereby yielding a single compound or a mixture having a desired purity or a desired composition. When the unreacted raw materials are left, they are recovered for recirculation to the reaction system. The catalyst employed are then reproduced or separated, as desired, for recirculation.

Further, the solvents or the materials employed together with the catalyst, particularly the cyclic ethers and so on constituting the components therefor, can be readily separated and recovered in conventional manner and recirculated as desired.

The carbonyl compounds yield in the process according to the present invention in the manner as described hereinabove can be employed appropriately in various fields including a synthetic chemistry field or the like, for example, as solvents, chemicals and so on.

Second Mode

Catalyst

The catalyst to be employed in the second preferred mode of the process according to the present invention is composed of the palladium compound, the polyoxoanion compound and a quinone and/or an aromatic diol.

It is to be noted herein that the palladium compound and the polyoxoanion compounds are the same as described hereinabove in the first preferred mode thereof, so that description thereof will be omitted from the following explanation.

The quinone to be employed is not restricted to a particular one as long as it has a quinone structure within its molecule.

As specific examples of the quinones, there may be mentioned 1,4-naphthoquinone, 1,2-naphthoquinone, methylnaphthoquinone, hydroxynaphthoquinone, 1,4-benzoquinone, 1,2-benzoquinone, methylbenzoquinone, dihydroxybenzoquinone, tetracyanobenzoquinone, dichlorodicyanobenzoquinone, anthraquinone, methylanthraquinone, acenaphthenequinone, and so on.

Among those quinones, 1,4-naththoquinone, 1,4-benzoquinone, anthraquinone and so on are preferred.

As the aromatic diols, various compounds may be employed without limitation as long as they are a reduced type compound of quinones, They may include, for example, hydroquinone, catechol, 1,4-dihydroxynaphthalene, 1,2-di-hydroxynaphthalene and so on.

In accordance with the present invention, the quinone and the aromatic diol may be employed singly or in combination of two or more or both of the quinone and the aromatic diol may be employed in a mixture.

The rate of the quinone and/or the aromatic diol employed for forming the catalyst, with respect to the palladium compound, may appropriately be selected in accordance with the kind of and the combination of the compounds to be employed therefor and it may be larger usually by 0.1 times in mole or more than 0.1 times in mole, preferably by from 1 to 20 times in mole, the quantity of the palladium compound.

The palladium compound, the polyoxoanion compound and the quinone and/or the aromatic diol may be fed in a mixture or separately to the reaction system.

The catalyst may optionally contain another promoting catalyst component including a ligand component as long as it does not adversely affect the objects of the present invention.

In the process according to the present invention, the catalyst may be employed in any state such as a homogeneous state, a heterogeneous state or a solid state or in a combination of those states. For example, the catalyst component may be employed in a homogeneous solution in which they are dissolved in a solvent, as will be described hereinafter, or in a heterogeneous solution in which a portion of the catalyst components are dissolved in the solvent while the rest of the catalyst components is dispersed therein, or in a solid state in which the catalyst components are deposited or fixed on a carrier such as active carbon, silica or the polymer.

Solvents

In accordance with the present invention, the carbonyl compounds are prepared by oxidizing the olefin with the aid of the catalyst in the presence of the solvent.

The solvent may be any organic solvent or a mixture of the organic solvent with water, as long as the objects of the present invention are not affected adversely.

The organic solvents may invlude, for example, a hydrocarboneous compound, a sulfur-containing organic compound, a nitrogen-containing organic compound and an oxygen-containing organic compound.

As the hydrocarboneous compounds, there may be mentioned, for example, a linear paraffinic hydrocarbon such as hexane, 2,2,5-trimethylhexane, heptane, octane, isooctane, nonane, decane, dodecand and so on, a cyclic paraffinic hydrocarbon such as cyclopentane, cyclohexane, methylcyclohexane, ethylcyclohexane and so on, an aromatic hydrocarbon such as benzene, toluene, xylene, ethylbenzene, cumene, mesitylene, tetralin, butylbenzene, p-cymene, cyclohexylbenzene, diethylbenzene, pentylbenzene, dipentylbenzene, dodecylbenzene and so on, and a halogenated organic compound such as dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, propyl chloride, isopropyl chloride, 1,2-dichloropropane, 1,2,3-trichloropropane, butyl chloride, sec-butyl chloride, tert-butyl chloride, 1-chloropentane, chlorobenzene, o-dichlorobenzene, m-dichlorobenzene, 1,2,4-trichlorobenzene, o-chlorotoluene, p-chlorotoluene, bromoform, 1,2-dibromoethane, 1,1,2,2-tetrabromoethane, propyl bromide, isopropyl bromide, bromobenzene, o-dibromobenzene, fluorobenzene, 1,1,2-trichloro-1,2,2-trifluoroethane, and so on.

As the sulfur-containing organic compounds, there may be mentioned, for example, thiophene, tetrahydrothiophene, dimethylsulfoxide, sulpholan and so on.

The nitrogen-containing organic compounds may include, for example, N,N-dimethylformamide, nitrobenzene, pyrrolidone and so on.

As the oxygen-containing organic compounds, there may be mentioned, for example, a monovalent alcohol having from 1 to about 6 carbon atoms, such as methanol, ethanol, n-propanol, isopropanol, n-butanol, sec-butanol, n-pentanol, n-hexanol and so on, a polyvalent alcohol having from 1 to about 6 carbon atoms, such as ethylene glycol, propylene glycol, diethylene glycol and so on, an ether such as 1,4-dioxane, tetrahydrofuran, ethyl ether, ethylene glycol dimethyl ether, diethylene glycol dimethyl ether and so on, a ketone such as acetone, methyl ethyl ketone, diethyl ketone and so on, and an ester such as γ-butyrolactone, δ-valerolactone and so on.

In accordance with the present invention, the oxygen-containing organic compounds are preferred among those as described hereinabove, and the alcohols and the ethers are particularly preferred.

The aforesaid organic solvents may be employed singly or in combination with two or more. Further, the organic solvents may contain another kind of solvents as long as they do not adversely affect the objects of the present invention.

The ratio of the solvent to be employed in accordance with the present invention may be in the range usually from 1 liter to nearly 1,000 liters to 1 mole of the palladium compound to be employed.

In accordance with the present invention, the solvent may be used together with water. The ratio of water to be solvent is not restricted to a particular one and water may be employed at an arbitrary ratio. Although the ratio of water cannot be determined in a uniform manner because it may vary with the kind of the catalyst or the catalyst components (the palladium compounds and the poloxoanion compounds), the kind of the raw olefins and the solvents, the reaction systems, the reaction conditions and so on, it can appropriately be determined with those aforesaid elements into account. If the ratio of the water content is too large, the palladium component may settle as a metallic palladium ($Pd^\circ$) or aggregate, thereby causing the likelihood to reduce the catalyst activity. As the solubility of the olefins as the raw materials in water is low, the problem may arise that the efficiency in the contact between the olefins and the catalyst (the solution having catalyst) becomes so low that no sufficient reaction rate can be achieved. With those points taken into account, the proportion of water to the total weight of the solvent may appropriately be usually 70% by weight or lower, preferably in the range from 0.5% to 50% by weight.

Olefins

The olefins to be employed in the second mode of the process according to the present invention are the same as in the first preferred mode thereof.

Oxidizing agents

The oxidizing agents to be employed in the second mode of the process according to the present invention are the same as in the first preferred mode thereof.

Oxidation

The oxidation to be employed in the second mode of the process according to the present invention is the same as in the first preferred mode thereof.

Reaction Product

Description of the reaction product obtainable in the second mode of the process according to the present invention is identical to that of the first preferred mode thereof.

In accordance with the first preferred mode of the process according to the present invention, the carbonyl compounds, such as the aldehydes and the ketones, can be produced stably with high reactivity and high yield in a remarkably mild condition by oxidizing the corresponding olefins because the catalyst is employed in the presence of the particular materials existing together with the catalyst, i.e. the solvents or the like, consisting of a mixture of water and the particular cyclic ether, not in the presence of water alone, in oxidizing the olefins with the aid of the catalyst system composed of the palladium compound and the polyoxoanion compounds such as the heteropolyacids or the isopolyacids. For example, ethylene yields acetaldehyde and propylene yields acetone. Further, methyl ethyl ketone is prepared from 1-butene or 2-butene, and cyclopentanone is prepared from cyclopentene. In addition, a higher olefin, an internal olefin or a cyclic olefin can be converted into the corresponding carbonyl compounds such as ketones or aldehydes.

Further, the first preferred mode of the process according to the present invention can remarkably improve the efficiency in the contact between the olefins as the raw materials and the catalyst components (the catalyst solution) when the oxidation is carried out in the liquid phase in which the the materials existing together with the catalyst, composed on the cyclic ethers and water, are employed as the solvents. Additionally, this process can effectively prevent the activity of the compounds employed as the catalyst from deteriorating due to sedimentation or conversion into an insoluble form or for other reasons. Furthermore, the first mode of the process according to the present invention can maintain the high reaction rate in a stable manner.

In other words, the first mode of the process according to the present invention can provide the process for preparing the carbonyl compounds, which is remarkably advantageous over the conventional processes. Hence, the process according to the present invention can sufficiently realize the industrial process that can produce the carbonly compounds from the corresponding olefins as well as it achieves improvements in the conventional process for preparing acetaldehyde from ethylene, acetone from propylene, and so on.

On the other hand, the second preferred mode of the process according to the present invention can remarkably improve the reactivty (TON) to the carbonyl compounds such as the ketones and aldehydes and, further, prevent the sedimentation of the catalyst components in an effective fashion, so that the catalyst activity can be maintained at a high level and in a stable manner for a long period of time, not only in the initial stage of reaction.

Hence, the second mode of the process according to the present invention can provide the process for preparing the useful carbonyl compounds in a stable fashion with high efficiency and productivity.

BEST MODE FOR CARRYING OUT THE INVENTION

The present invention will be described more in detail by way of working examples with reference to comparative examples.

It is to be noted herein, however, that the present invention should not be interpreted in any respect as being restricted to the following examples and it should be construed as encompassing various modifications and changes within the scope and spirit of the present invention.

EXAMPLE 1

An autoclave was charged with a solution of 0.4 mmol (0.0955 gram) of $PdSO_4 \cdot 2H_2O$ and 1.8 mmol (3.52 grams; water content, 13.3% by weight) of $H_6PV_3Mo_9O_{40}$ in 25 ml. of 1,4-dioxane and 5 ml of water, and 216 mmol of trans-2-butene was oxidized with oxygen at 97° C. for 35 minutes while the total pressure was held at 10 kg/cm² (gauge pressure) by supplying oxygen, thereby yielding methyl ethyl ketone (MEK) in the quantity of 100.5 mmol. In this case, the quantity (in mol) of the MEK produced per mol of palladium, i.e., the TON of the MEK, was 431 mol/(mol.hour). No undissolved materials, such as sediment, were found in the reaction solution after completion of the reaction.

EXAMPLE 2

The procedures of Example 1 were followed in substantially the same manner, except for using 0.2 mmol(0.0478 g) OF $PdSO_4.2H_2O$ and setting the reaction temperature to 79° C., the reaction time to 70 minutes and the reaction pressure (total presssure) to 8 kg/cm² (gauge pressure).

This example gave MEK in the quantity of 92.3 mmol. This yield corresponds to the TON of the MEK at 396 mol/(mol.hour). In this case, no undissolved materials, such as precipitats (sedments), were found in the reaction solution after the reaction had been finished.

COMPARATIVE EXAMPLE 1

The procedures were followed in substantially the same manner as in Example 2, except for using 10 ml of acetonitrile and 30 ml of water, in place of 25 ml of 1,4-dioxane and 5 ml of water, additionally using 2 mmol (0.501 gram) of $CuSO_4.5H_2O$ as a metal component, and setting the reaction pressure (total pressure) to 9 kg/cm² (gauge pressure).

This example yielded MEK in the quantity as low as 39.7 mmol, and this yield corresponds to the TON of the MEK at 85 mol/(mol.hour). Further, black precipitates, presumably Pd black, were recovered in the quantity of 44.0 mg from the reaction mixture after completion of the reaction.

EXAMPLE 3

The procedures were performed in substantially the same manner as in Example 1, except for setting the reaction temperature to 58° C., the reaction time to 120 minutes and the reaction pressure (total pressure) to 6 kg/cm² (gauge pressure).

As a result, MEK was yielded in the quantity of 88.8 mmol. This yield corresponds to the TON of the MEK at 111 mol/(mol.hour). In this example, no undissolved materials, such as precipitates, were found in the reaction mixture after the reaction has been finished.

EXAMPLE 4

The procedures were followed in substantially the same manner as in Example 3, except for using 1.8 mmol (3.88 grams; water content, 23.7% by weight) of $H_7PV_4Mo_8O_{40}$, in place of $H_6PV_3Mo_9O_{40}$.

This example yielded MEK in the quantity of 79.2 mmol, and this yield corresponds to the TON of the MEK at 99 mol/(mol.hour). No undissolved materials, such as precipitates, were found in the reaction mixture after the completion of the reaction.

COMPARATIVE EXAMPLE 2

The procedures were followed in substantially the same manner as in Example 4, except for using 10 ml of tetrahydrofuran (THF) and 20 ml of water, in place of 25 ml of 1,4-dioxane and 5 ml of water.

This example yielded MEK in the quantity as low as 40 mmol, and this yield corresponds to the TON of the MEK at 51 mol/(mol.hour). Further, black precipitates, presumably Pd black, were recovered in the quantity of 5 mg from the reaction mixture after completion of the reaction.

COMPARATIVE EXAMPLE 3

The procedures were followed in substantially the same manner as in Example 4, except for using 30 ml of water, in place of 25 ml of 1,4-dioxane and 5 ml of water.

This example yielded MEK in the quantity as remarkably low as 3 mmol, and this yield corresponds to the TON of the MEK at 4 mol/(mol.hour). Further, black precipitates, presumably Pd black, were recovered in the quantity of 87.2 mg from the reaction mixture after completion of the reaction.

EXAMPLE 5

An autoclave was charged with a solution of 0.21 mmol (0.0499 gram) of $PdSO_4. 2H_2O$ and 1.8 mmol (3.52 grams; water content, 13.3% by weight) of $H_6PV_3Mo_9O_{40}$ in 15 ml of 1,4-dioxane and 15 ml of water, and 225 mol of trans-2-butene was oxidized with oxygen at 76° C. for 70 minutes while the total pressure was held at 9 kg/cm² (gauge pressure) by supplying oxygen, thereby yielding methyl ethyl ketone (MEK) in the quantity of 100.5 mmol.

This yield corresponds to the TON of the MEK at 293 mol/(mol.hour). No. undissolved materials, such as sediment, were found in the reaction solution after completion of the reaction.

EXAMPLE 6

The procedures were followed in substantially the same manner as in Example 5, except for using 10 ml of 1,4-dioxane and 20 ml of water, in place of 15 ml of 1,4-dioxane and 15 ml of water.

This example gave MEK in the quantity of 55.7 mmol. This yield corresponds to the TON of the MEK at 223 mol/(mol.hour). In this case, no undissolved materials, such as precipitats, were found in the reaction solution after the reaction had been finished.

EXAMPLE 7

A Pyrex reactor was charged with a solution of 0.80 mmol (0.1907 gram) of $PdSO_4.2H_2O$ and 4.2 mmol (9.08 grams; water content, 23.7% by weight) of $H_7PV_4Mo_8O_{40}$ in 50 ml of 1,4-dioxane and 10 ml of water, and the mixture was heated in an oil bath of 50° C. In this state, propylene and oxygen were supplied to the solution within the reactor at normal pressure at the rates of 40 cc per minute and 20 cc per minute, respectively, and the oxidation was continued for 1 hour.

As a result, acetone was yielded in the quantity of 58.4 mmol. In this case, the quantity (in mol) of acetone produced per mol of palladium for the reaction time of 1 hour corresponds to the TON of the acetone at 78 mol/(mol.hour). No undissolved materials, such as sediment, were found in the reaction solution after completion of the reaction. This continuous system has the advantages that costs of equipment can be lowered and the period of time required for production can be shortened.

EXAMPLE 8

A Pyrex reactor was charged with a solution of 0.20 mmol (0.0477 gram) of $PdSO_4.2H_2O$ and 4.2 mmol (9.08 grams; water content, 23.7% by weight) of $H_7PV_4Mo_8O_{40}$ in 50 ml of 1,4-dioxane and 10 ml of water, and the mixture was heated in an oil both of 50° C. In this state, 1-octene was supplied in the quantity of 100 mmol (11.2 grams) and oxygen was then supplied to the solution within the reactor at normal pressure at the rate of 60 cc per minute. The oxidation was carried out in this state for 1 hour.

As a result, 2-octanone was yielded in the quantity of 22.0 mmol. In this case, the quantity (in mol) of 2-octanone produced per mol of palladium for the reaction time of 1 hour corresponds to the TON of the octanone at 110 mol/(mol.hour). No undissolved materials, such as precipitates, were found in the reaction solution after completion of the reaction.

EXAMPLE 9

An autoclave was charged with a solution of 0.2 mmol (0.0482 gram) of $PdSO_4.2H_2O$ and 1.8 mmol (3.52 grams; water content, 13.3% by weight) of $H_6PV_3Mo_9O_{40}$ in 25 ml of 2-methyl-1,3-dioxolan and 5 ml of water, and 225 mmol of trans-2-butene was oxidized with oxygen at 76° C. for 60 minutes at the pressure of 9 kg/cm$^2$ (gauge pressure) by supplying oxygen, thereby yielding MEK in the quantity of 71.4 mmol. This yield corresponds to the TON of the MEK at 357 mol/(mol.hour). No undissolved materials, such as sediment, were found in the reaction solution after completion of the reaction.

EXAMPLE 10

An autoclave was charged with a solution of 0.20 mmol (0.0482 gram) of $PdSO_4.2H_2O$ and 1.8 mmol (3.52 grams; water content, 13.3% by weight) of $H_6PV_3Mo_9O_{40}$ in 25 ml of 1,4-dioxane and 5 ml of water, and 147 mmol (10.0 grams) of cyclopentene was added to the solution. Thereafter, the pressure within the autoclave was elevated to 8.5 kg/cm$^2$ (gauge pressure) by supplying nitrogen at 60° C. and then to the total pressure of 10 kg/cm$^2$ (gauge pressure) by supplying oxygen. The reaction was carried out in this state for 120 minutes at the pressure of 10 kg/cm$^2$ (Gauge pressure) by supplying oxygen.

As a result, cyclopentanone and 2-cyclopenten-1-one were yielded in the quantities of 11.2 mmol and 8.7 mmol, respectively. No undissolved materials, such as sediment, were found in the reaction solution after completion of the reaction.

EXAMPLE 11

An autoclave was charged with a mixture (dispersion solution) of 1.001 grams of 5% by weight Pd/Carbon and 1.8 mmol (3.52 grams; water content, 13.3% by weight) of $H_6PV_3Mo_9O_{40}$ in 25 ml of 1,4-dioxane and 5 ml of water, and 225 mmol of 1-butene was oxidized with oxygen at 79° C. for 120 minutes at the pressure of 8 kg/cm$^2$ (gauge pressure) by supplying oxygen, thereby yielding MEK in the quantity of 54.1 mmol. This yield corresponds to the TON of the MEK at 78 mol/(mol.hour). This heterogeneous system has the advantage that separation operations are simple.

EXAMPLE 12

The procedures of Example 2 were followed in substantially the same manner, except for using 1-butene as raw olefin.

This example yielded MEK in the quantity of 90.4 mmol, and this yield corresponds to the TON of the MEK at 387 mol/(mol.hour). No undissolved materials such as precipitate were found in the reaction mixture after the completion of the reaction.

EXAMPLE 13

The procedures of Example 1 were followed in substantially the same manner, except for using 0.2 mmol(0.0608 g) of Pd(acac)$_2$ instead of using 0.4 mmol(0.0955 g) of $PdSO_4.2H_2O$, setting the reaction temperature to 77° C. and setting the reaction time to 90 minutes.

This example yielded MEK in the quantity of 102.4 mmol, and this yield corresponds to the TON of the MEK at 512 mol/(mol.hour). No undissolved materials such as precipitate were found in the reaction mixture after the completion of the reaction.

EXAMPLE 14

The procedures of Example 1 were followed in substantially the same manner, except for using 0.2 mmol(0.0453 g) of Pd(NO$_3$)$_2$ instead of using 0.4 mmol(0.0955 g) of $PdSO_4.2H_2O$, setting the reaction temperature to 77° C. and setting the reaction time to 90 minutes.

This example yielded MEK in the quantity of 66.9 mmol, and this yield corresponds to the TON of the MEK at 223 mol/(mol.hour). No undissolved materials such as precipitate were found in the reaction mixture after the completion of the reaction.

EXAMPLE 15

A solution containing 0.7 mmol of $[V_8Mo_4O_{36}]^{-8}$ was obtained by mixing water solution composed 10 ml of water and 20 ml of 1,4-dioxane with 0.68 g of NaVO$_3$ and 0.67 g of Na$_2$MoO$_4$19 2H$_2$O and adding sulfuric acid in order to adjusting pH of the solution to 1.6. An autoclave was charged with a mixture of said solution and 0.1 mmol (0.0239 g) of $PdSO_4.2H_2O$. In the autoclave 226 mmol of trans-2-butene was oxidized with oxygen at 79° C. for 120 minutes while the total pressure was held at 8 kg/cm$^2$ (gauge pressure) by supplying oxygen.

Thereby MEK was yield int he quantity of 21.3 mmol, and this yield corresponds to the TON of the MEK at 107 mol/(mol.hour). No undissolved materials such as precipitate were found in the reaction mixture after the completion of the reaction.

EXAMPLE 16

The procedures of Example 2 were followed in substantially the same manner, except for using 1.8 mmol(4.421 g, content of water;11.2% by weight) of $H_6PV_3W_9O_{40}$ in place of $H_6PV_3Mo_9O_{40}$ and setting the reaction temperature to 90 minutes.

This example yielded MEK in the quantity of 50.1 mmol, and this yield corresponds to the TON of the MEK at 167 mol/(mol.hour). No undissolved materials such as precipitate were found int he reaction mixture after the completion of the reaction.

EXAMPLE 17

An autoclave was charged with a mixture of 1.0 mmol (0.1590 gram) of 1,4-naphthoquinone with a solution of 0.4 mmol (0.0955 gram) of $PdSO_4.2H_2O$ and 1.8 mmol (3.8808 grams; water content, 23.5% by weight) of $H_7PV_4Mo_8O_{40}$ in 25 ml of 1,4-dioxane and 5 ml of water, and 200 mmol of trans-2-butene was oxidized with oxygen at 50° C. for 2 hours at the pressure of 6 kg/cm$^2$ (gauge pressure) by supplying oxygen, thereby yielding MEK in the quantity of 80.0 mmol. This yield corresponds to the TON (turn-over number) of 100 based on Pd. No undissolved materials, such as sediment, were recovered from the reaction solution after completion of the reaction.

It is to be noted that the TON referred to herein is intended to mean the quantity (in mol) of the MEK produced per unit of Pd per unit time (in hour).

EXAMPLE 13

The procedures were followed in substantially the same manner as in Example 17, except for adding 1,4-naphthoquinone in the quantity of 10.0 mmol (1.5900 grams).

The results are shown in Table below.

EXAMPLE 19

An autoclave was charged with a mixture of 10.0 mmol (1.5900 grams) of 1,4-naphthoquinone with a solution of 0.2 mmol (0.0478 gram) of $PdSO_4.2H_2O$ and 1.8 mmol (3.5155 grams; water content, 13.3% by weight) of $H_6PV_3Mo_9O_{40}$ in 25 ml of 1,4-dioxane and 5 ml of water, and 200 mmol of trans-2-butene was oxidized with oxygen at 80° C. for 1 hour at the pressure of 8 kg/cm$^2$ (gauge pressure) by supplying oxygen. The results are shown in Table below.

EXAMPLE 20

The procedures were followed in substantially the same manner as in Example 17, except for using tetrahydrofuran in place of 1,4-dioxane. The results are shown in Table below.

EXAMPLE 21

The procedures were followed in substantially the same manner as in Example 17, except for using 30 ml of ethanol, in place of 25 ml of 1,4-dioxane and 5 ml of water and setting the reaction time to 1 hour. The results are shown in Table below.

EXAMPLE 22

An autoclave was charged with a mixture of 1.0 mmol (0.1590 gram) of 1,4-naphthoquinone with a solution of 0.2 mmol (0.0478 gram) of $PdSO_4.2H_2O$ and 1.8 mmol (3.8808 grams; water content, 23.5% by weight) of $H_7PV_4Mo_8O_{40}$ in 30 ml of ethylene glycol and 5 ml of water, and 200 mmol of trans-2-butene was oxidized with oxygen at 50° C. for 1 hour at the pressure of 6 kg/cm$^2$ (gauge pressure) by supplying oxygen. The results are shown in Table below.

EXAMPLE 23

The procedures were followed in substantially the same manner as in Example 22, except for using 4.0 mmol (0.6360 gram) of 1,4-naphthoquinone. The results are shown in Table below.

EXAMPLE 24

The procedures were followed in substantially the same manner as in Example 22, except for using 1.0 mmol (0.2082 gram) of anthraquinone, in place of 1,4-naphthoquinone, and setting the reaction time to 2 hours. The results are shown in Table below.

EXAMPLE 25

The procedures were followed in substantially the same manner as in Example 22, except for using 0.5 mmol (0.0795 gram) of 1,4-naphthoquinone, using 1-butene in place of trans-2-butene, and holding the pressure at 7 kg/cm$^2$ (gauge pressure) by supplying oxygen. The results are shown in Table below.

EXAMPLE 26

The procedures were followed in substantially the same manner as in Example 17, except for using 28 ml of MEK and 2 ml of water, in place of 25 ml of 1,4-dioxane and 5 ml of water. The results are shown in Table below.

EXAMPLE 27

The procedures were followed in substantially the same manner as in Example 17, except for using γ-butyrolactone, in place of 1,4-dioxane. The results are shown in Table below.

EXAMPLE 28

An autoclave was charged with a mixture of 1.0 mmol (0.1590 gram) of 1,4-naphthoquinone with a solution of 0.4 mmol (0.0955 gram) of $PdSO_4.2H_2O$ and 1.8 mmol (3.8808 grams; water content, 23% by weight) of $H_7PV_4Mo_8O_{40}$ in 30 ml of ethylene glycol and 5 of water, and 147 mmol of cyclopentene was oxidized with oxygen-containing gases ($N_2/O_2=77/15$) at 50° C. for 2 hours at the pressure of 10 kg/cm$^2$ (gauge pressure) by supplying oxygen. The results are shown in Table below.

EXAMPLE 29

The procedures were followed in substantially the same manner as in Example 28, except for increasing the quantity of 1,4naphthoquinone to 2.0 mmol (0.3180 grams). The results are shown in Table below.

EXAMPLE 30

A flask was charged with a solution of 0.8 mmol (0.1910 gram) of $PdSO_4.2H_2O$, 4.2 mmol (9.0552 grams; water content, 23.5% by weight) of $H_7PV_4Mo_8O_{40}$, and 8.0 mmol (1.2720 grams) of 1,4-naphthoquinone in 50 ml of 1,4-dioxane and 10 ml of water, and propylene and oxygen were fed at the rates of 40 ml per minute and 20 ml per minute, respectively, and propylene was oxidized with oxygen at 50° C. for the 2 hours. The results are shown in Table below.

EXAMPLE 31

A solution was prepared by dissolving 0.2 mmol (0.0478 gram) of $PdSO_4.2H_2O$, 4.2 mmol (9.0552 grams; water content, 23.5% by weight) of $H_7PV_4Mo_8O_{40}$, 8.0 mmol (0.8648 gram) of 1,4-benzoquinone, and 100 mmol of 1-octene in 50 ml of 1,4-dioxane and 10 ml of water, and oxygen was fed at the rate of 60 ml per minute, and 1-octene was oxidized with oxygen at 50° C. for 1 hour. The results are shown in Table below.

COMPARATIVE EXAMPLE 4

An autoclave was charged with a mixture of 2.0 mmol (0.4999 gram) of $CuSO_4.5H_2O$ with a solution of 0.4 mmol (0.0955 gram) of $PdSO_4.2H_2O$ and 1.8 mmol (3.8808 grams; water content, 23.5% by weight) of $H_7PV_4Mo_8O_{40}$ in 10 ml of acetonitrile and 30 ml of water, and 200 mmol of trans-2-butene was oxidized with oxygen at 50° C. for 2 hours at the pressure of 6 kg/cm$^2$ (gauge pressure) by supplying oxygen. The results are shown in Table below.

COMPARATIVE EXAMPLE 5

An autoclave was charged with a mixture of 1.0 mmol (0.1590 gram) of 1,4-naphthoquinone with a solution of 0.4 mmol (0.0709 gram) of $PdCl_2$ and 2.0 mmol (0.3410 gram) of $CuCl_2.2H_2O$ in 25 ml of N-methylpyrrolidone and 5 ml of water, and 200 mmol of trans-2-butene was oxidized with oxygen at 50° C. for 2 hours at the pressure of 6 kg/cm² (gauge pressure) by supplying oxygen. The results are shown in Table below.

COMPARATIVE EXAMPLE 6

An autoclave was charged with a mixture of 1.0 mmol (0.1590 gram) of 1,4-naphthoquinone with a solution of 0.4 mmol (0.0709 gram) of $PdCl_2$ and 2.0 mmol (0.3410 gram) of $CuCl_2.2H_2O$ in 30 ml of ethanol, and 200 mmol of trans-2-butene was oxidized with oxygen at 50° C. for 2 hours at the pressure of 6 kg/cm² (gauge pressure by supplying oxygen. The results are shown in Table below.

COMPARATIVE EXAMPLE 7

An autoclave was charged with a mixture of 1.0 mmol (0.1590 gram) of 1,4-naphthoquinone with a solution of 0.4 mmol (0.0955 gram) of $PdSO_4.2H_2O$ and 2.0 mmol (0.4657 gram, $VOSO_4$; 70%) of $VOSO_4.xH_2O$ in 30 ml of ethanol, and 200 mmol of trans-2-butene was oxidized with oxygen at 50° C. for 2 hours at the pressure of 6 kg/cm² (gauge pressure) by supplying oxygen. The results are shown in Table below.

EXAMPLE 32

The procedures of Example 19 were followed in substantially the same manner, except for using $Pd(NO_3)_2$ in place of using of $PdSO_4.2H_2O$.

This example yielded MEK int he quantity of 61.6 mmol, and this yield corresponds to the TON of the MEK at 308 mol/(mol.hour). No undissolved materials such as precipitate were found in the reaction mixture after the completion of the reaction.

EXAMPLE 33

The procedures of Example 21 were followed in substantially the same manner, except for using $Pd(CH_3COO)_2$ in place of using of $PdSO_4.2H_2O$.

This example yielded MEK int he quantity of 96.4 mmol, and this yield corresponds to the TON of the MEK at 241 mol/(mol.hour). No undissolved materials such as precipitate were found in the reaction mixture after the completion of the reaction.

EXAMPLE 34

The procedures of Example 22 were followed in substantially the same manner, except for using 1.8 mmol (5.0117 g, content of water; 15.5% by weight) of $H_3PMo_6W_6O_{40}$ in place of $H_7PV_4Mo_8O_{40}$.

This example yielded MEK in the quantity of 40.1 mmol, and this yield corresponds to the TON of the MEK at 201 mol/(mol.hour). No undissolved materials such as precipitate were found in the reaction mixture after the completion of the reaction.

EXAMPLE 35

A solution containing 0.7 mmol of $[V_8Mo_4O_{36}]^{-8}$ was obtained by mixing water solution having 10 ml of water and 20 ml of 1,4-dioxane with 0.68 g of $NaVO_3$ and 0.67 g of $Na_2MoO_4.2H_2O$ and adding sulfuric acid in order to adjusting pH of the solution of 1.6. An autoclave was charged with a mixture of said solution, 0.1 mmol(0.0239 g) of $PdSO_4.2H_2O$ and 10.0 mmol of 1,4-naphtoquinone. In the autoclave 200 mmol of trans-2-butene was oxidized with oxygen at 80° C. for 120 minutes while the total pressure was held at 8 kg/cm² (gauge pressure) by supplying oxygen.

Thereby MEK was yielded in the quantity of 33.9 mmol, and this yield corresponds to the TON of the MEK at 170 mol/(mol.hour). No undissolved materials such as precipitate were found in the reaction mixture after the completion of the reaction.

TABLE

| | Solvent | Reaction Time (hr) | Product | Amount of Product (mmol) | TON (mol/ mol-Pd. hr) | Amount of Sediment Recovered (g) |
|---|---|---|---|---|---|---|
| Example 18 | 1,4-dioxane + water | 2 | MEK | 93.8 | 117 | None |
| Example 19 | 1,4-dioxane + water | 1 | MEK | 104.2 | 521 | None |
| Example 20 | tetrahydrofuran + water | 2 | MEK | 73.6 | 92 | None |
| Example 21 | ethanol | 1 | MEK | 113.5 | 284 | None |
| Example 22 | ethylene glycol + water | 1 | MEK | 61.4 | 307 | None |
| Example 23 | ethylene glycol + water | 1 | MEK | 71.3 | 357 | None |
| Example 24 | ethylene glycol + water | 2 | MEK | 82.4 | 206 | None |
| Example 25 | ethylene glycol + water | 1 | MEK | 57.8 | 289 | None |
| Example 26 | MEK + water | 2 | MEK | 71.7 | 90 | None |
| Example 27 | γ-butyrolactone + water | 2 | MEK | 70.4 | 88 | None |
| Example 28 | ethylene glycol + water | 2 | cyclopentanone | 29.8 | 37 | None |
| Example 29 | ethylene glycol + water | 2 | cyclopentanone | 41.8 | 52 | None |
| Example 30 | 1,4-dioxane + water | 2 | acetone | 126.4 | 79 | None |
| Example 31 | 1,4-dioxane + water | 1 | 2-octane | 38.1 | 191 | None |
| Comparative Ex. 4 | acetonitrile + water | 2 | MEK | 50.7 | 63 | 0.0838 |
| Comparative Ex. 5 | N-methylpyrrolidone + water | 2 | MEK | 3.9 | 5 | 0.0087 |
| Comparative Ex. 6 | ethanol | 2 | MEK | 16.1 | 20 | 0.0066 |
| Comparative Ex. 7 | ethanol | 2 | MEK | 2.5 | 3 | 0.0103 |

We claim

1. A process for preparing a carbonyl compound which comprises oxidizing 1-10,000 mols of an olefin having from 2 to 20 carbon atoms at a temperature of 0°-700° C. in the presence of a catalyst and a solvent;
   said catalyst being composed of one mole of active metallic palladium or a palladium compound and a polyoxoanion compound containing as its metal component at least one metal selected from the group consisting of V, Mo, W, Nb and Ta;
   said solvent comprising water and a cyclic ether selected from the group consisting of 1,4-dioxane, alkyl-substituted 1,4-dioxane, 1,3-dioxolan and alkyl-substituted 1,3-dioxolan; said solvent containing 5-70% by weight of water.

2. A process for preparing a carbonyl compound as in claim 1, wherein the palladium compound is at least one of palladium sulfate, palladium acetylacetonate and palladium nitrate.

3. A process for preparing a carbonyl compound as in claim 1, wherein the polyoxanion is at least one of a heterpolyoxanion and an isopolyoxanion.

4. A process for preparing a carbonyl compound as in claim 3, wherein the heteropolyoxoanion is at least one of $H_6[PV_3MO_9O_{40}]$ and $H_7[PV_4MO_8O_{40}]$.

5. A process for preparing a carbonyl compound as in claim 1, wherein the cyclic ether is at least one of 1,4-dioxane and 2-methyl-1,3-dioxolan.

6. A process for preparing a carbonyl compound as claimed in claim 1, wherein the olefin contains from 2 to 10 carbon atoms.

7. A process for preparing a carbonyl compound which comprises oxidizing 1-10,000 moles of an olefin having from 2 to 20 carbons at a temperature of 0°-700° C. in the presence of a catalyst composed of one mole of active metallic palladium or a palladium compound, a polyoxanion compound containing as its metal component one or more metals selected from the group consisting of V, Mo, W, Nb and Ta; and a solution containing at least one quinone selected from the group consisting of 1,4-naphthoquinone, 1,2-naphthoquinone, methylnaphthoquinone, hydroxynaphthoquinone, 1,4-benoquinone, 1,2-benzoquinone, methybenzoquinone, dihydroxybenzoquinone, tetracycanobenzoquinone, dichlorodicyanobenzoquinone, anthraquinone, methylanthraquinone and acenaphthenequinone, or corresponding reduced quinone.

8. A process for preparing a carbonyl compound as in claim 7, wherein the palladium compound is palladium sulfate.

9. A process for preparing a carbonyl compound as in claim 7, wherein the polyoxanion is a heteropolyoxanion compound.

10. A process for preparing a carbonyl compound as in claim 9, wherein the heteropolyoxoanion compound is at least a member selected from a group consisting of $H_6[PV_3MO_9O_{40}]$ and $H_7[PV_4MO_8O_{40}]$.

11. A process for preparing a carbonyl compound as in claim 7, wherein the quinone is at least a member selected from the group consisting of 1,4-naphthoquinone, 1,4-benzoquinone and anthraquinone.

12. A process for preparing a carbonyl compound as in claim 7, wherein the olefin is a cycloalkene or a linear olefin having from 2 to 10 carbon atoms.

* * * * *

UNITED STATES PATENT AND TRADEMARK OFFICE
CERTIFICATE OF CORRECTION

PATENT NO.: 5,237,103
DATED      : August 17, 1993
INVENTOR(S): SAITO et al.

It is certified that error appears in the above-identified patent and that said Letters Patent is hereby corrected as shown below:

On the cover page, Item [73], "Kemitsu Kosan Company Limited" should read --Idemitsu Kosan Company Limited--.

Signed and Sealed this

Twenty-fifth Day of July, 1995

Attest:

BRUCE LEHMAN

Attesting Officer

Commissioner of Patents and Trademarks